(12) United States Patent
Lee et al.

(10) Patent No.: US 12,708,551 B2
(45) Date of Patent: Aug. 18, 2026

(54) ORAL DEVICE

(71) Applicants: Seung Hee Lee, Hanam-si (KR); Edwards Kyoung-joon Mun, Natick, MA (US)

(72) Inventors: Seung Hee Lee, Hanam-si (KR); Edwards Kyoung-joon Mun, Natick, MA (US)

( * ) Notice: Subject to any disclaimer, the term of this patent is extended or adjusted under 35 U.S.C. 154(b) by 212 days.

(21) Appl. No.: 17/496,172

(22) Filed: Oct. 7, 2021

(65) Prior Publication Data

US 2022/0023092 A1 Jan. 27, 2022

Related U.S. Application Data

(63) Continuation of application No. PCT/KR2019/004958, filed on Apr. 24, 2019.

(30) Foreign Application Priority Data

Apr. 9, 2019 (KR) ........................ 10-2019-0041515

(51) Int. Cl.
*A61F 5/56* (2006.01)
*A61B 13/00* (2006.01)

(52) U.S. Cl.
CPC .............. *A61F 5/566* (2013.01); *A61B 13/00* (2013.01)

(58) Field of Classification Search
CPC . A61F 5/566; A61F 5/56; A61B 13/00; A61B 1/24; A61B 5/4818; A61B 5/4815; A63B 23/032; A61M 16/0495; A61M 16/049; A61M 1/00; A61M 2210/0637; A61C 5/90; A61C 7/08
USPC .................................................. 128/858, 848
See application file for complete search history.

(56) References Cited

U.S. PATENT DOCUMENTS

| | | | | |
|---|---|---|---|---|
| 11,033,421 | B1 * | 6/2021 | Davis | A61F 5/566 |
| 2005/0224444 | A1 | 10/2005 | Akihiro | |
| 2010/0043804 | A1 | 2/2010 | Razmovski | |
| 2011/0232651 | A1 * | 9/2011 | Diers | A61F 5/566 128/848 |
| 2017/0000694 | A1 * | 1/2017 | Lee | A61J 11/006 |
| 2017/0106267 | A1 * | 4/2017 | Garner | A61M 16/0493 |
| 2017/0151086 | A1 * | 6/2017 | Fareid | A61F 5/566 |
| 2018/0263809 | A1 * | 9/2018 | Masuda | A61F 5/566 |
| 2019/0059714 | A1 * | 2/2019 | Choi | A61C 8/00 |
| 2019/0380863 | A1 * | 12/2019 | Mauclaire | A61F 5/566 |

FOREIGN PATENT DOCUMENTS

| | | | |
|---|---|---|---|
| JP | 2005-296117 | A | 10/2005 |
| JP | 4035574 | B2 | 1/2008 |
| JP | 2008-67732 | A | 3/2008 |

(Continued)

*Primary Examiner* — Ophelia A Hawthorne
*Assistant Examiner* — Michael Milo
(74) *Attorney, Agent, or Firm* — United One Law Group LLC; Kongsik Kim; Jhongwoo Peck

(57) ABSTRACT

An oral device includes a body, which is configured to be disposed inside an oral cavity. The oral device also includes at least one wing which can push at least one of palatoglossus or palatopharyngeus outward. Further, the body can also be configured to be disposed to downwardly press a tongue to relax intrinsic tongue muscles, thereby pushing the tongue rearward and moving soft palate downward. Accordingly, the oral device is able to open nasopharynx.

9 Claims, 31 Drawing Sheets

(56) References Cited

FOREIGN PATENT DOCUMENTS

| | | | | | |
|---|---|---|---|---|---|
| JP | 2014158607 | A | * | 9/2014 | ............... A61N 1/36 |
| JP | 5858549 | B1 | | 2/2016 | |
| JP | 2016-93397 | A | | 5/2016 | |
| KR | 10-2006-0012065 | A | | 2/2006 | |
| KR | 10-2012-0033385 | A | | 4/2012 | |
| KR | 20120033385 | A | * | 4/2012 | |
| KR | 10-1463021 | B1 | | 11/2014 | |
| KR | 10-2017-0109439 | A | | 9/2017 | |
| KR | 10-1832858 | B1 | | 2/2018 | |
| KR | 101944807 | B1 | * | 2/2019 | ............. A61C 5/007 |
| KR | 10-2106780 | B1 | | 5/2020 | |
| WO | WO-0180762 | A2 | * | 11/2001 | ............... A61C 7/08 |
| WO | 2006/063403 | A1 | | 6/2006 | |

* cited by examiner

ORAL DEVICE

CROSS-REFERENCE TO RELATED APPLICATION

The present application is a Continuation of International Application No. PCT/KR2019/004958 filed on Apr. 24, 2019, which claims priority to Korean Application No. 10-2019-0041515 filed on Apr. 9, 2019. The aforementioned applications are incorporated herein by reference in their entireties.

TECHNICAL FIELD

The present disclosure relates to an oral device. In particular, the present disclosure relates to an oral device which enables a user to easily breathe through the nasopharynx.

RELATED ART

When a person breathes, especially in sleep, the cheek muscles move inward; and the mouth is closed and moves forward. In that situation, the soft palate and the extrinsic tongue muscles cannot function normally. Further, the tongue moves forward and upward, and the mouth opens, thereby making it difficult to breathe through the nose.

In that situation, the soft palate cannot move toward the tongue, and the floor of mouth cannot move toward the palate. Thus, the soft palate closes the nasopharynx so that the fauces which is connected to the oropharynx cannot be normally closed. Consequently, the person breathes through the mouth, not through the nose, thereby causing hypoxia, apnea, snoring, otitis media, a deformation of dental arrangement due to a wrong movement of the tongue, mental distraction, dysphonia, and the like.

Because of an imbalance between the muscles which connect the face, the mouth, and the pharynxes, athletes also have troubles of breathing through the nasopharynx so that the athletes cannot bring out the maximum athletic performance they have.

SUMMARY

Accordingly, the present disclosure has been made in view of the above-mentioned problems occurring in the prior art, and it is an object of the present disclosure to provide an oral device solving the problems the prior arts have.

The object of the present disclosure is to provide an oral device which prevents air from inadvertently going into the stomach and prevents saliva from inadvertently going into the lungs, thereby preventing the problems caused by those situations. Another object of the present disclosure is to provide an oral device which allows the facial muscles, the oral muscles, and the muscles connecting the pharynxes to normally function, thereby providing orthodontics.

To accomplish the above-mentioned object, according to the present disclosure, there is provided an oral device which comprises a body to be disposed inside the oral cavity and at least one wing configured to push cheek muscles outward.

The oral device can further comprise a connecting portion which is connected to the body.

The connecting portion can be configured to prevent the tongue from moving upward so as to relax intrinsic tongue muscles.

The body can be separated into at least two parts.

The body can be integral with at least one of the wings and the connecting portion.

At least a portion of the body can conform to the teeth arrangements.

The body can comprise a tooth receiver which receives at least a portion of tooth.

The body can comprise a first portion which is provided in the upper tooth and a second portion which is provided in the lower tooth. The first portion and the second portion can be connected to each other to prevent the lips from opening.

The first portion and the second portion can be connected at front side of the oral cavity The oral device can further comprise a fastener to be fastened to a liquid container and a passageway through which liquid passes.

An oral device of another aspect of the present disclosure comprises a body, at least a portion of which is disposed inside the oral cavity. The body is configured to press the tongue to relax intrinsic tongue muscles.

The oral device can further comprise a connecting handle which is connected to the body.

The connecting portion can be disposed outside the oral cavity.

The connecting device can be disposed inside the oral cavity; and is convex upward or downward.

The body can comprise a side body which is configured to be disposed on the side of tooth outside of the tooth; an inner extending portion which extends inwardly from the side body to be engaged with upper tooth and lower tooth; and at least one wing which laterally extends from the side body to push cheek muscles outward.

The oral device can further comprise a connecting portion which connects the side bodies.

The inner extending portion can be configured to press the tongue, thereby relaxing intrinsic tongue muscles.

According to the oral device of the present disclosure, the corrective and proper muscle transition is induced and the breathing through the nasopharynx is easily achieved.

The corrective and proper muscle transition means pushing the cheek muscle outward to prevent the lips from pushing forward, thereby preventing the soft palate from closing the nasopharynx. The transition relaxes the intrinsic tongue muscle and activates the extrinsic tongue muscle to prevent the tongue from moving forward and upward; makes the floor of mouth go toward the palate; and makes the soft palate go toward the tongue to close the fauces, thereby achieving the breathing through nasopharynx, not through the oropharynx in any situation.

The oral device of the present disclosure relieves apnea, breathing disorders, snoring, otitis media, deformation of dental arch due to the incorrect movement of the tongue, distractions, dysphonia, gas pain, decreased athletic performance and the like.

BRIEF DESCRIPTION OF DRAWINGS

The present disclosure will be more fully understood from the following detailed description taken in conjunction with the accompanying drawings.

Figure 1:
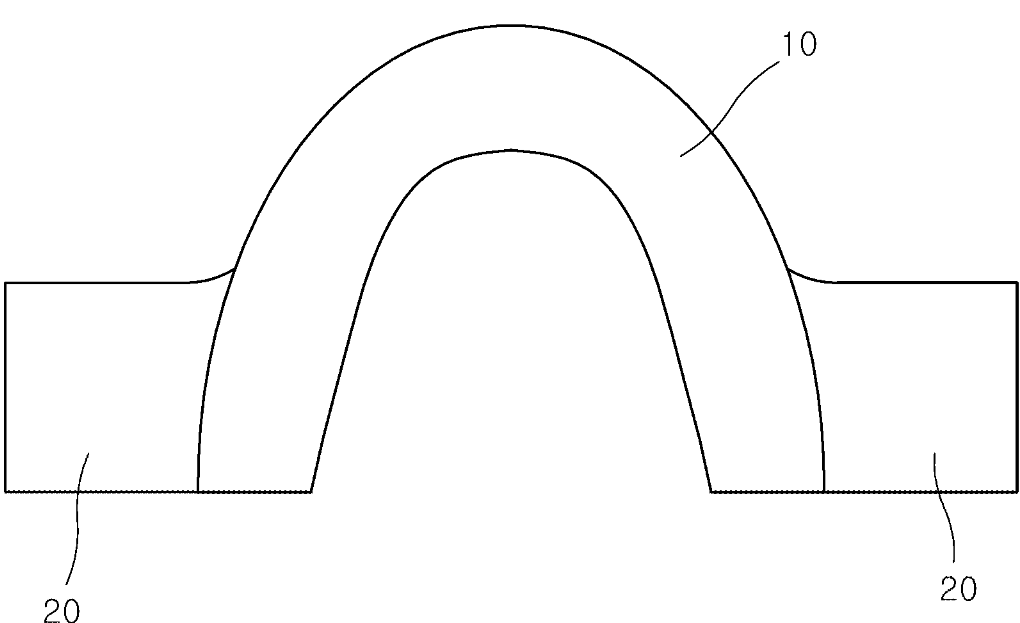
FIGS. 1 to 10 are the plan views of the various oral devices of the present disclosure.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Hereinafter, the present disclosure will be described in detail with reference to the accompanying drawings. As those skilled in the art would realize, the described embodiments may be modified in various different ways, all without departing from the spirit or scope of the present disclosure.

In this specification, the essential elements for the present disclosure will be described and the non-essential elements may not be described. However, the scope of the present disclosure should not be limited to the invention including only the described components. Further, it should be understood that the invention which includes additional element or does not have non-essential elements can be within the scope of the present disclosure.

The terms "first," "second," or the like are herein used to distinguishably refer to same or similar elements, or the steps of the present disclosure and they may not infer an order or a plurality.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The term "or" in this specification is defined to indicate at least one of a plurality of elements, not to indicate any one of a plurality of the elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

The term "coupled" or "connected" denotes a physical relationship between two components whereby the components are either directly connected to one another or indirectly connected via one or more intermediary components.

The "oral device" encompasses any device that can be configured to be placed in the oral cavity. For example, the oral device can be a pacifier, a straw, an anti-snoring device, an intermediary device for drinking beverage, an apnea corrector, a device for correcting oral habit, an orthodontic appliance, a functional mouthpiece, a sport mouthpiece, a discharger which can be placed in the oral cavity and the like.

In this specification, "upward" means a palate side; "downward" means a tongue side; "forward" means a forward side of the lips; and "rearward" means a fauces side.

FIG. 1 is a plan view of an oral device of the present disclosure. As shown in FIG. 1, the oral device of the present disclosure comprises a body (10), and at least one wing (20) which laterally extends from the body (10) to be configured to push the cheek muscles outward. At least a portion of the body (10) can be configured to be in contact with the user's tooth or not.

Although the wing (20) is illustrated to extend from both sides of the body (20), the wing (20) can extend from only one side of the body (10). Further, the extending range can be determined according to requirements.

Figure 2:
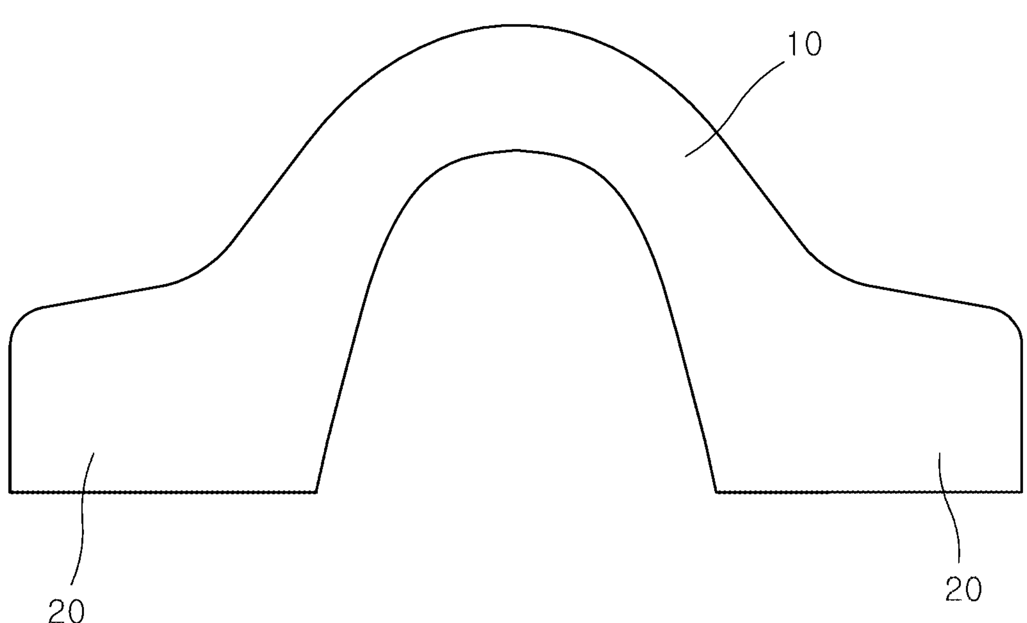

The body (10) and the wing (20) can be the separate elements from each other as shown in FIG. 1. Alternatively, they can be integral as shown in FIG. 2.

Figure 3:
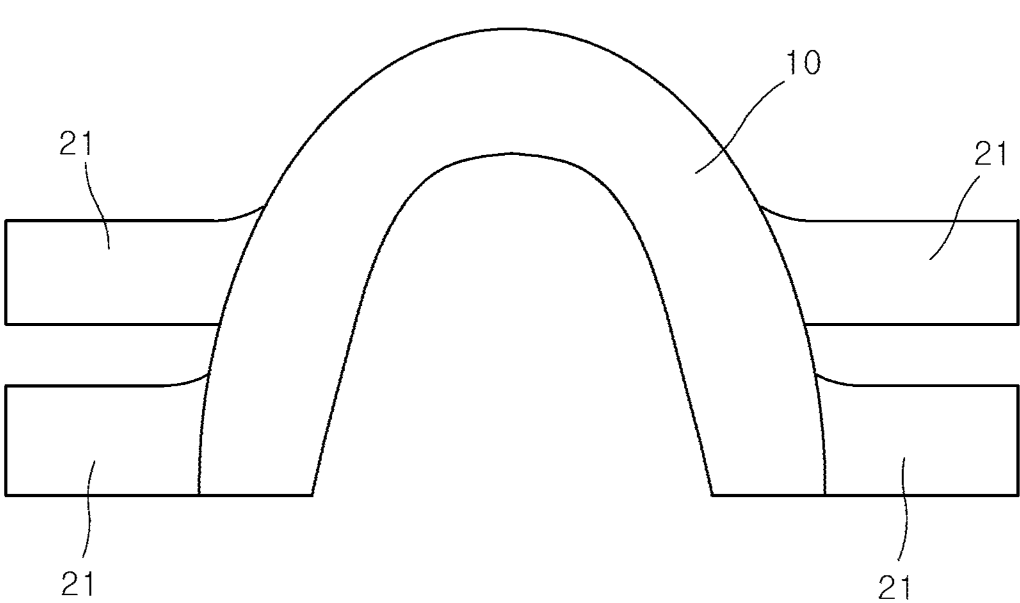
Figure 4:
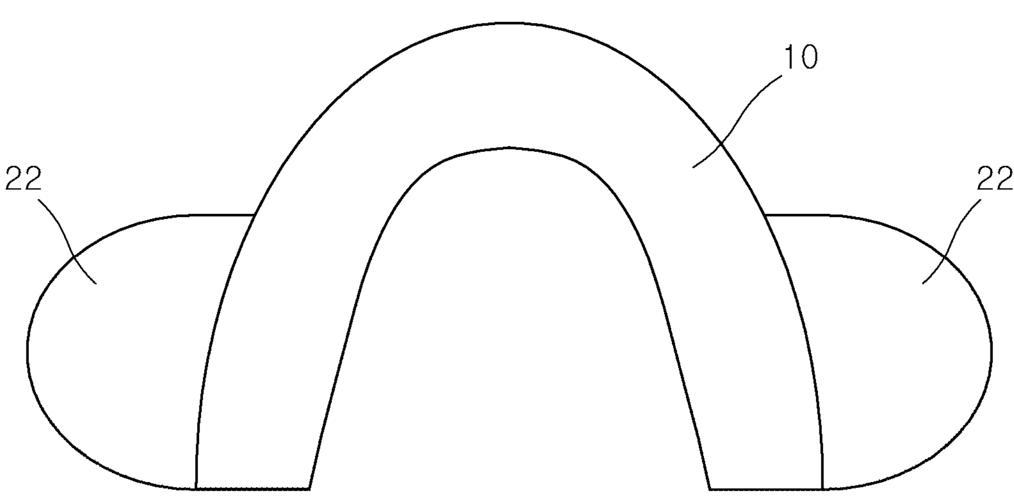

The wing (20) can have a plurality of wing portions as shown in FIG. 3.

The wing (20) can have any configuration that can push the cheek muscles outward. The wing (20), the ends of which have a round shape, can provide the user with the soft contacting feel with the inner muscle of the cheek.

Figure 20:
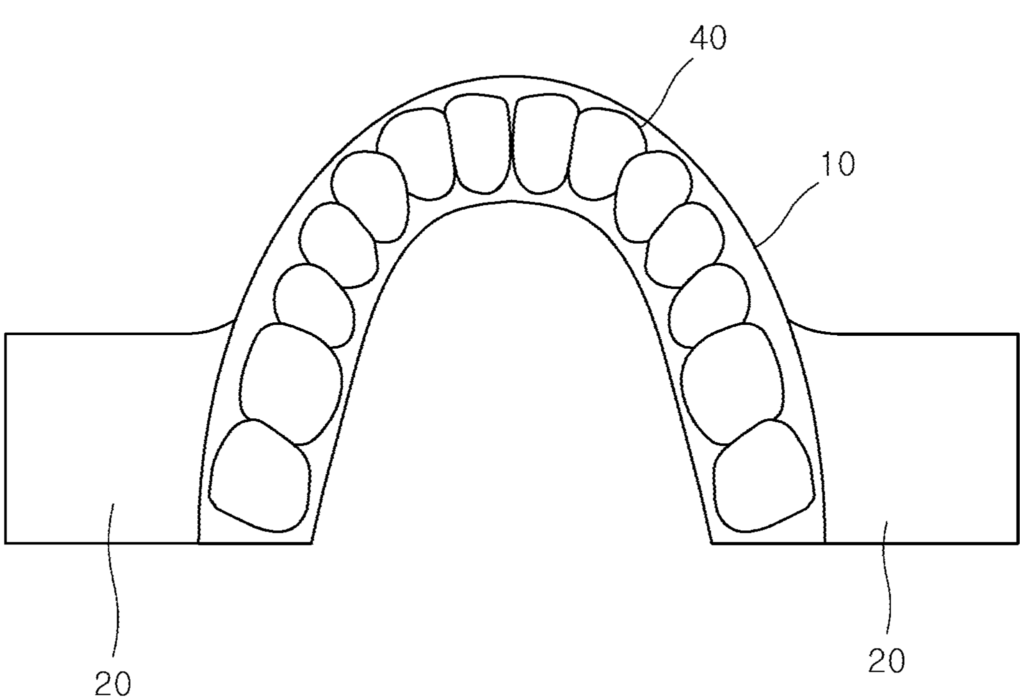
FIG. 20 is a plan view of the oral device modified from the oral device of FIG. 1.
Figure 21:
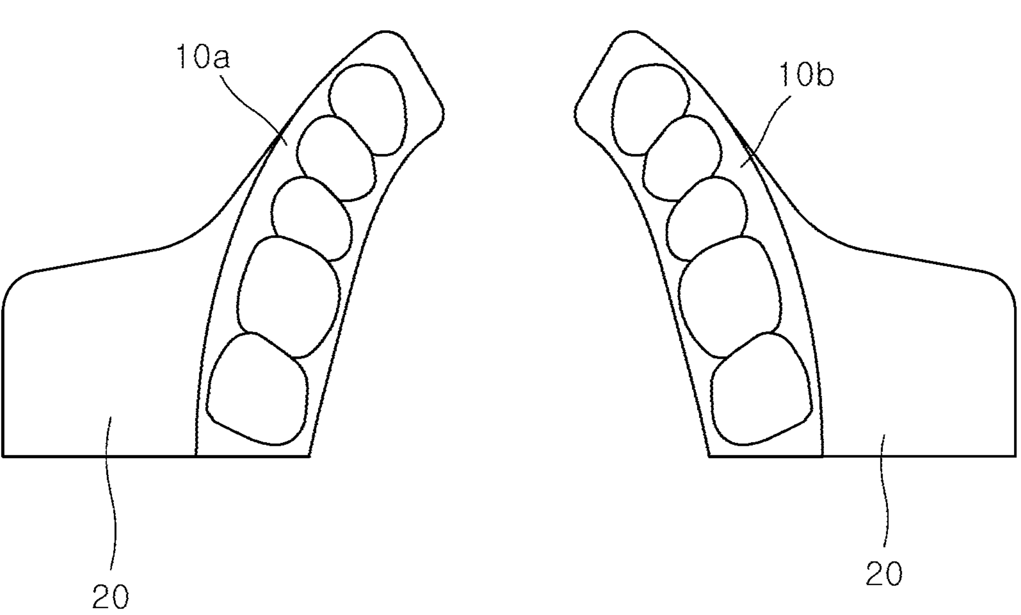
FIG. 21 is a plan view of the oral device modified from the oral device of FIG. 6.

At least a portion of the body (10) can have configuration which conforms to the teeth arraignments. Alternatively, the body (10) can comprise a tooth receiver (40) which receives at least a portion of the tooth as shown in FIG. 20. The tooth receiver (40) can receive all the upper teeth and all the lower teeth or can receive at least a portion of the teeth, for example, rearward teeth.

A material which can be deformed to conform to the shape of the tooth when the teeth are engaged and then can form a receiver that naturally conforms to the shape of the tooth, for example, a dental impression, can be attached to the body (10). Alternatively, the body (10) can be made of the material. In that case, the tooth receiver (40) can be formed when the tooth presses the body (10).

Figure 5:
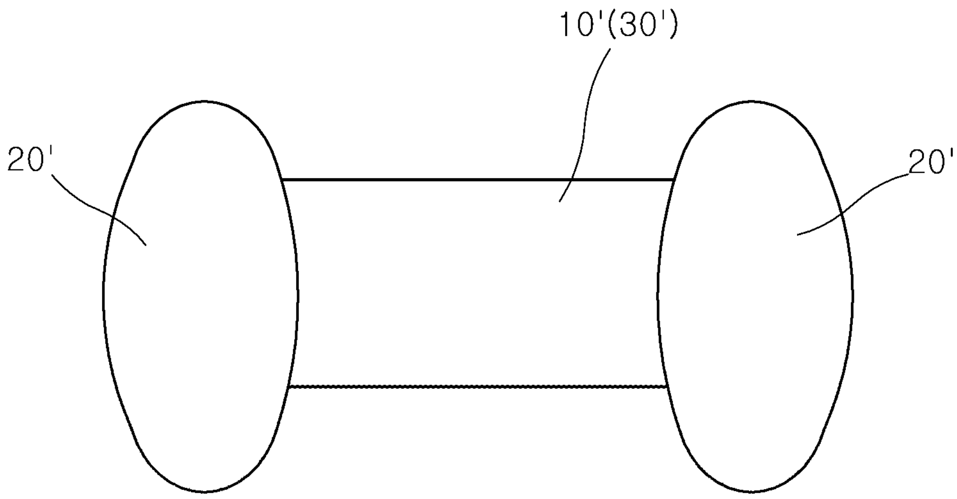

FIG. 5 shows a plan view of an oral device, the body of which does not conform to the teeth arrangements. The oral device of FIG. 5 comprises a body (10') and wings (20'). The body (10') does not conform to the teeth arrangements unlike the oral device of FIGS. 1 and 2. The wings (20') are provided in both sides of the body. In the embodiments, the body (10') can act as a role of the connecting portion which will be described in the below.

Although the body (10') is illustrated as a rectangle and the wings (20') are illustrated as ellipse, the shapes of the body (10') and the wings (20') can be a polygon or other shapes which cannot be geometrically defined. The width or the thickness of the front side and the rear side of the body (10') can be different to each other.

Figure 6:
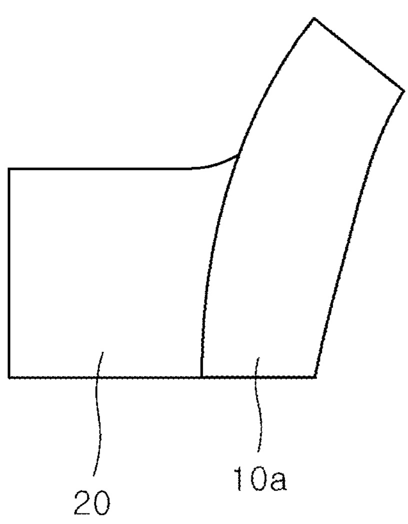
Figure 6:
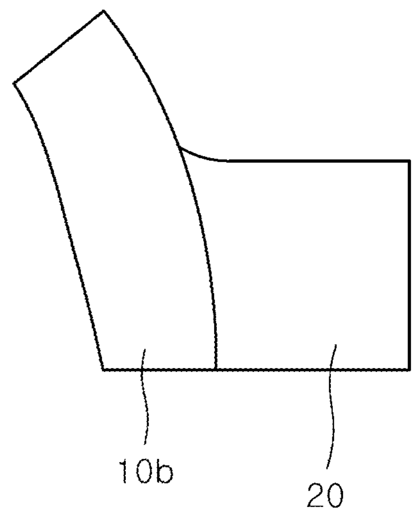

The body (10) can be separated into two portions (10*a*, 10*b*) as shown in FIG. 6. The wings (20) can extend from each separated portion (10*a*, 10*b*). The wing (20) can extend from only one of the separated portions although it is illustrated in FIG. 6 that the wings extend from each separated portion.

Figure 22:
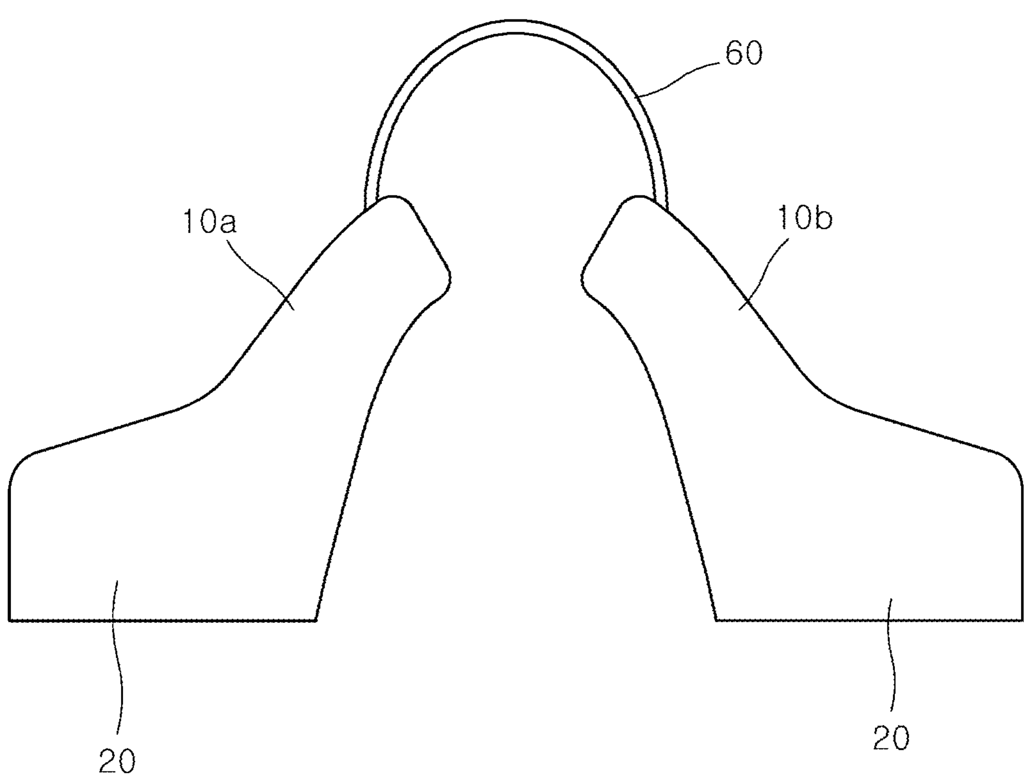
FIG. 22 is a plan view of the oral device modified from the oral device of FIG. 2.

FIG. 22 shows the embodiments that the body (10) is integral with the wing (20), but the body (10) are separated. The separated portions (10*a*, 10*b*) can be connected by the connecting strap (60). The connecting portion (30) shown in FIG. 7 can be additionally provided in the embodiments wherein the connecting strap (60) connects the separated portions (10*a*, 10*b*). The connecting strap (60) can be connected to an external element, for example, a user's clothing or a helmet. The connecting strap (60) can be provided to connect the separate bodies (10*a*, 10*b*) shown in FIG. 6. The connecting strap (60) can be made of a soft material or a hard material.

When the wing (20) pushes the side muscles of a cheek outward in the oral cavity, the lips are laterally extended; the tongue is relaxed rearward; and the soft palate moves down, thereby opening the nasopharynx. Therefore, the breathing through the nasopharynx is facilitated, thereby, for example, preventing saliva from going into the lungs or going behind a nose; and significantly relieving hypoxia, apnea, the problems caused by the breathing through oropharynx, tongue constriction, snoring, otitis media and the like. Further, the breathing through the nasopharynx can lead to a maximum athletic performance. The wing (20) can push, for example, the palatoglossus muscle or the palatopharyngeus muscle, outwardly.

Figure 8:
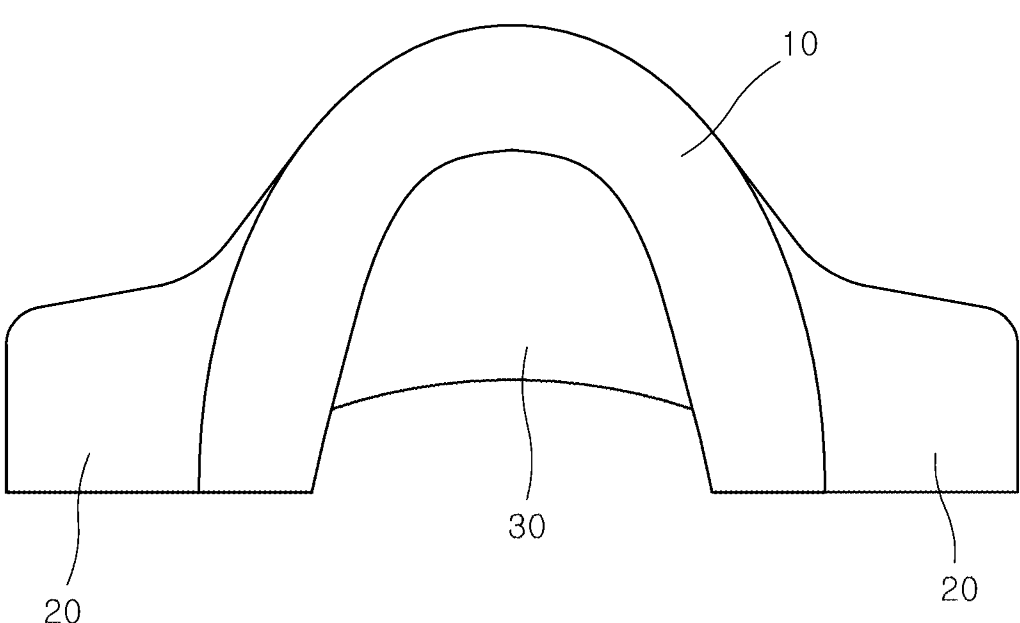
Figure 9:
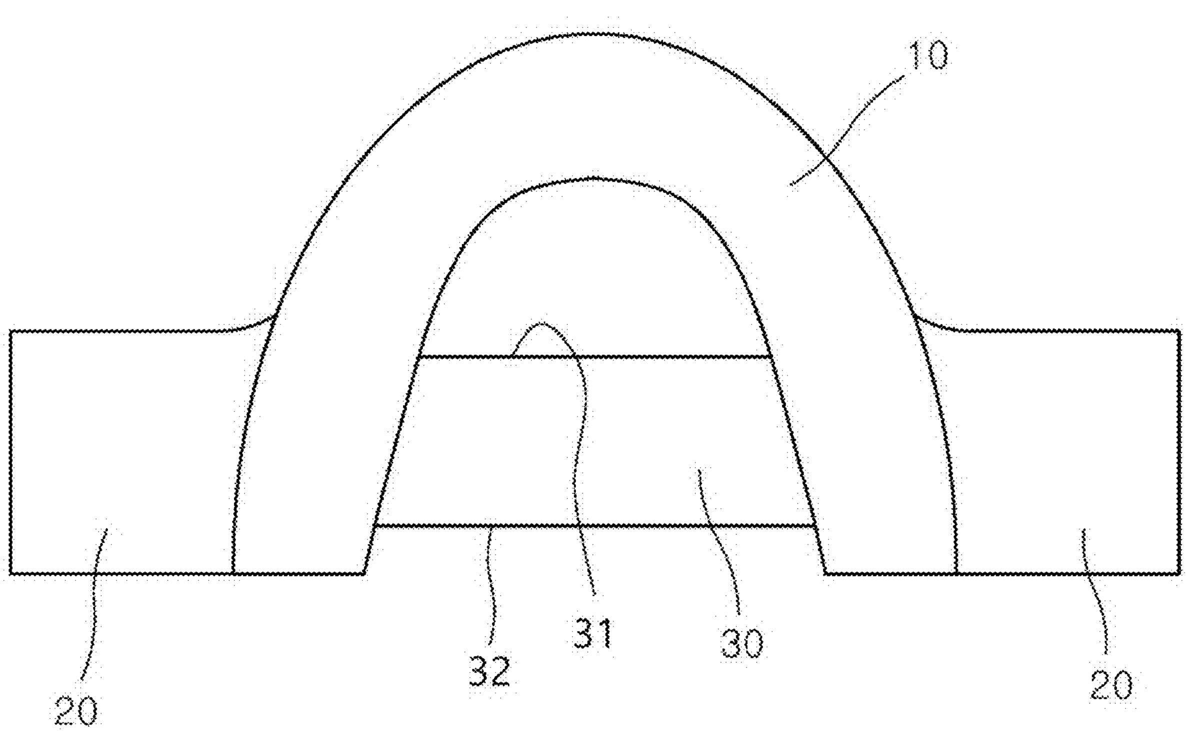

FIG. 8 is a plan view of an oral device according to a different aspect of the present disclosure. The oral device of FIG. 8 is different from the oral devices of FIGS. 1, 2, 3 and 4 in that the connecting portion (30) is provided. The connecting portion (30) can be provided to fill an inner space of the body (10) as shown in FIG. 8. Alternatively, the connecting portion (30) can be provided in a bridge form to connect the inner side of the body (10) as shown in FIG. 9. The connecting portion (30) can be provided in a form of a connecting strap as shown in FIG. 22. The position and the form of the connecting portion can be variously determined according to requirements. The connecting portion (30) can be made of a flexible material. The connecting portion (30) can be convex upward or downward.

Figure 7:
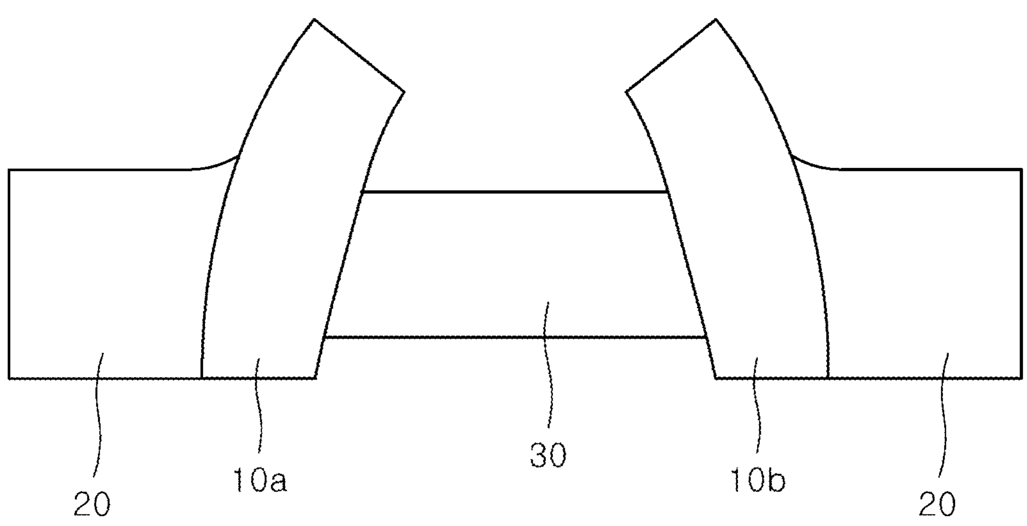
Figure 10:
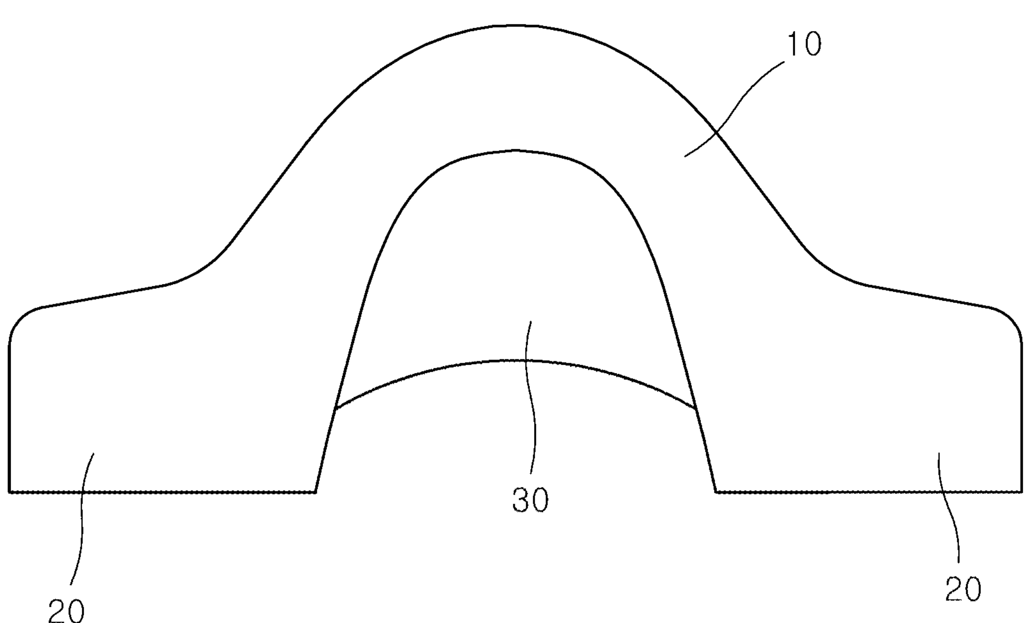

FIG. 7 shows a plan view of an oral device wherein a connecting portion (30) is provided in the embodiments that the body (10) is separated into the two portions; and FIG. 10 shows a plan view of an oral device wherein the connecting portion (30) is provided in the embodiments that the body (10) and the wing (20) are integral.

The connecting portion (30) which is disposed in the oral cavity can press the tongue, thereby relaxing the intrinsic tongue muscles. However, the connecting portion (30) which is disposed in the oral cavity may not press the tongue.

At least a portion of the connecting portion (30) can be contact with the upper side of the tongue to prevent the intrinsic tongue muscles from constricting, thereby preventing the tongue from moving forward or upward. When the intrinsic tongue muscles constrict and the tongue moves upward, the side muscles of the cheek are depressed, and the lips moves forward, thereby opening the oropharynx.

In that situation, the breathing through the nasopharynx becomes difficult, thereby causing the afore-mentioned problems, for example, going down the wrong pipe, gas pain caused by air entry to the stomach, and the like. When the connecting portion (30) presses the tongue, the extrinsic tongue muscles push the tongue rearward; the soft palate moves downward; the floor of mouth moves upward; and the facues are closed, thereby facilitating the breathing through the nasopharynx.

The connecting portion (30) which relaxes the intrinsic tongue muscles, prevents the tongue muscles from constricting, and prevents the cheek muscles from being depressed, thereby facilitating the breathing through the nasopharynx due to the corrective and proper muscle transition.

The effects of the present disclosure can be more amplified according to the constitution wherein the wing (20) pushes the side muscles of the cheek outward to prevent the soft palate from closing the nasopharynx; and the connecting portion (30) directly presses the tongue so that the extrinsic tongue muscles lower the soft palate, and the floor of mouth moves upward, thereby closing the oropharynx.

The connecting portion (30) can be configured not to press the tongue. As shown in FIG. 22, the connecting portion (30) can just connect the separated bodies (10*a*, 10*b*). Alternatively, the connecting portion (30) can be a member attached to an unseparated body (10).

The thickness of the connecting portion (30) can be uniform or not. In the embodiments shown in FIG. 9, the forward portion (31) and the rearward portion (32) can have the same thickness or not. The thickness of the connecting portion (30) can be the same as those of the body (10) and/or the wing (20), or not.

Figure 11:
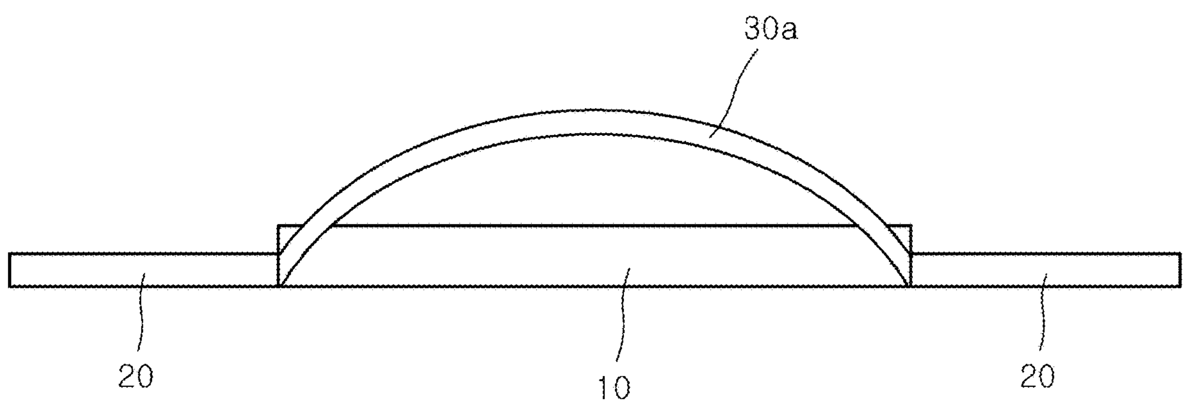
FIGS. 11 to 16 are the drawings of the various embodiments of the connecting portions shown in FIGS. 8 and 9.
Figure 12:
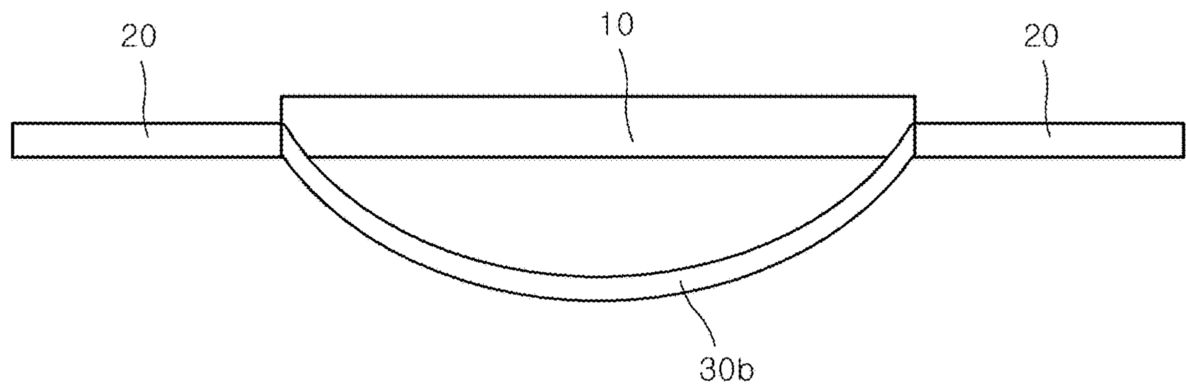
Figure 13:
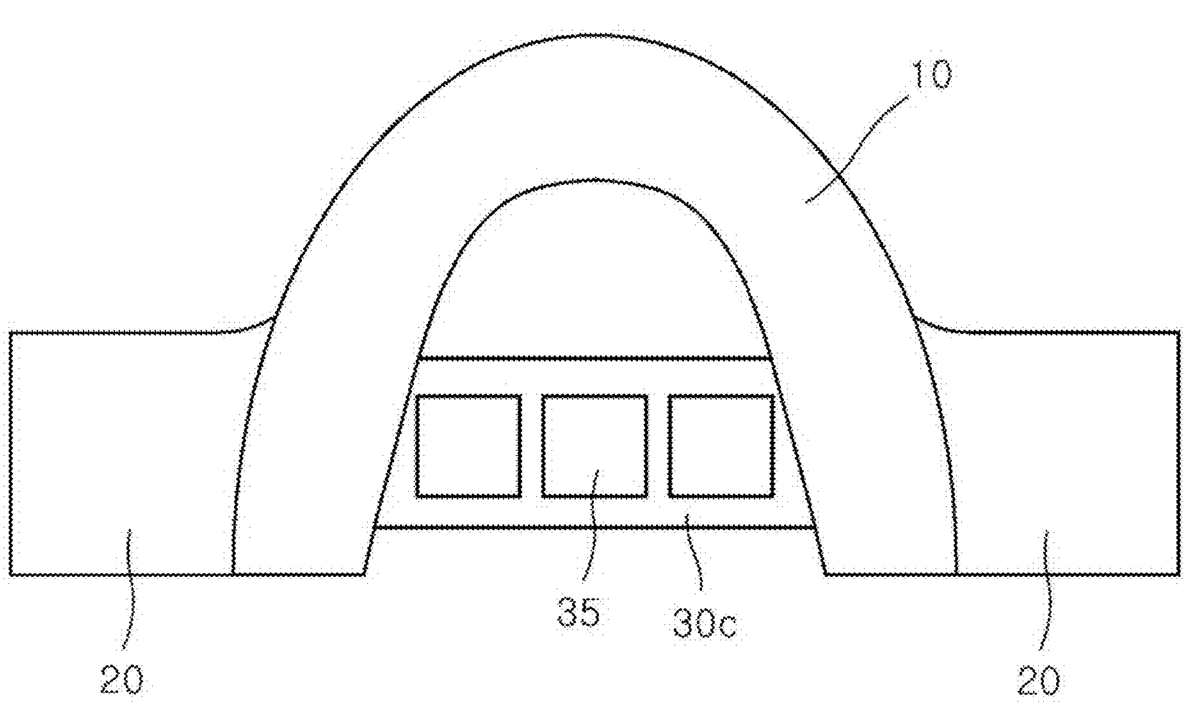
Figure 14:
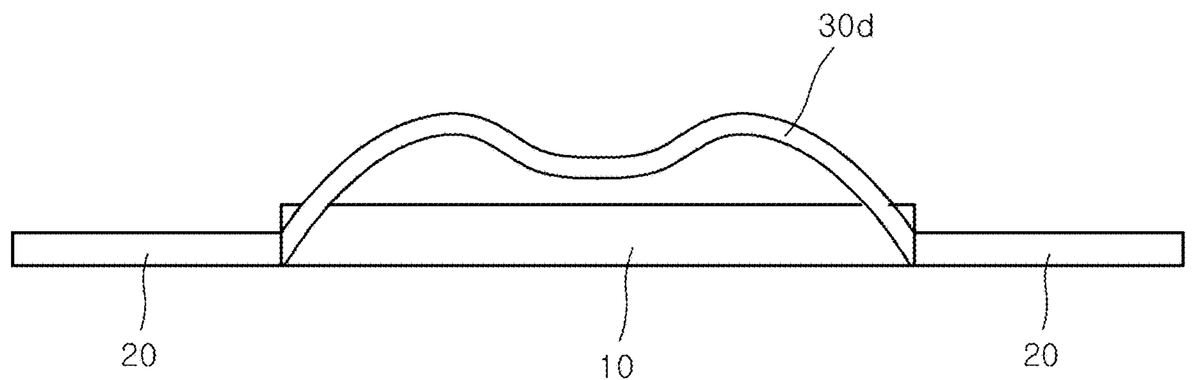
Figure 15:
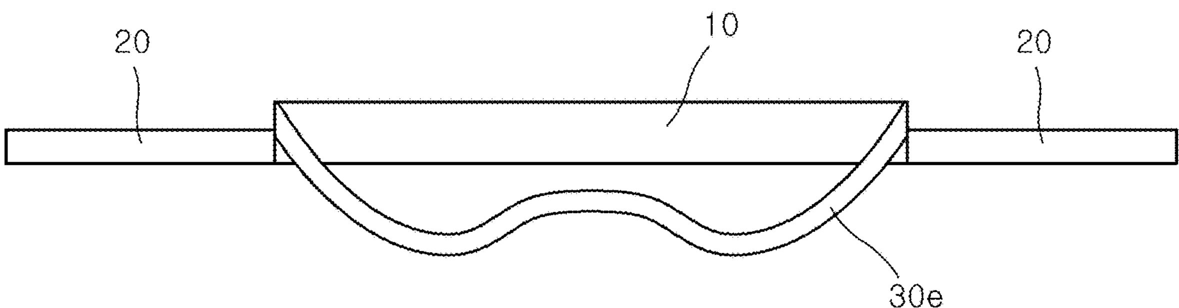
Figure 16:
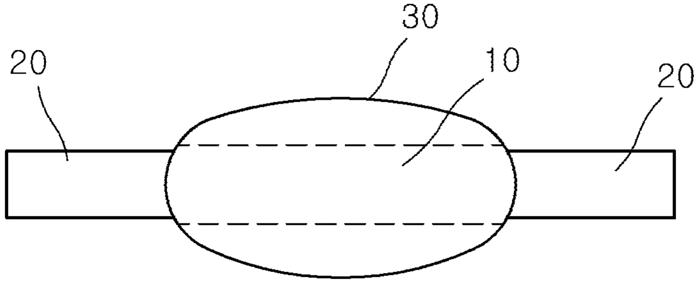

FIG. 11 shows a connecting portion (30*a*) which is upwardly convex; FIG. 12 shows a connecting portion (30*b*) which is downwardly convex; FIG. 13 shows a connecting portion (30*c*) which has a hole (35) formed thereon; FIG. 14 shows a connecting portion (30*d*) which is upwardly convex and is corrugated; and FIG. 15 shows a connecting portion (30*e*) which is downwardly convex and is corrugated. FIG. 16 shows a bottom view of an oral device wherein the cross section of the connecting portion (30) has an elliptic form. The curvature, the thickness, and the like of the bent connecting portion (30) can be variously determined according to requirements.

The hole (35) formed in the connecting portion (30) can relive the wearer's stuffiness and salivation. Although the hole (35) is illustrated as a rectangle in FIG. 13, the hole (35) can have any shape such as a polygon, a circle, an ellipse, a shape which cannot be geometrically defined and the like.

Figure 17:
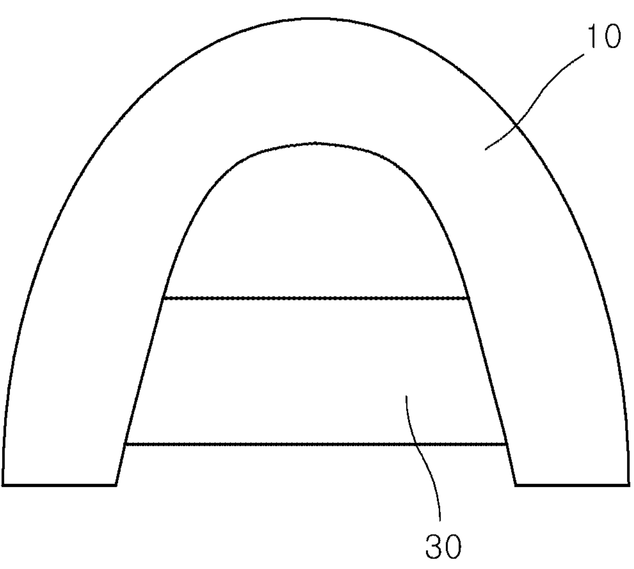
FIGS. 17 and 18 are the plan views of the oral device according to an embodiment of the present disclosure.

FIG. 17 shows a plan view of an oral device according to a different aspect of the present disclosure. The oral device comprises a body (10) and a connecting portion (30) but does not have a wing (20).

The oral device of FIG. 17 does not push the inner muscles of the cheek outward but relaxes the intrinsic tongue muscles to prevent the lips from moving forward so that the inner muscles of the cheek move outward; the floor of mouth moves upward; the soft palate moves downward, thereby closing the oropharynx. Thus, the oral device can also facilitate the breathing through the nasopharynx.

Figure 18:
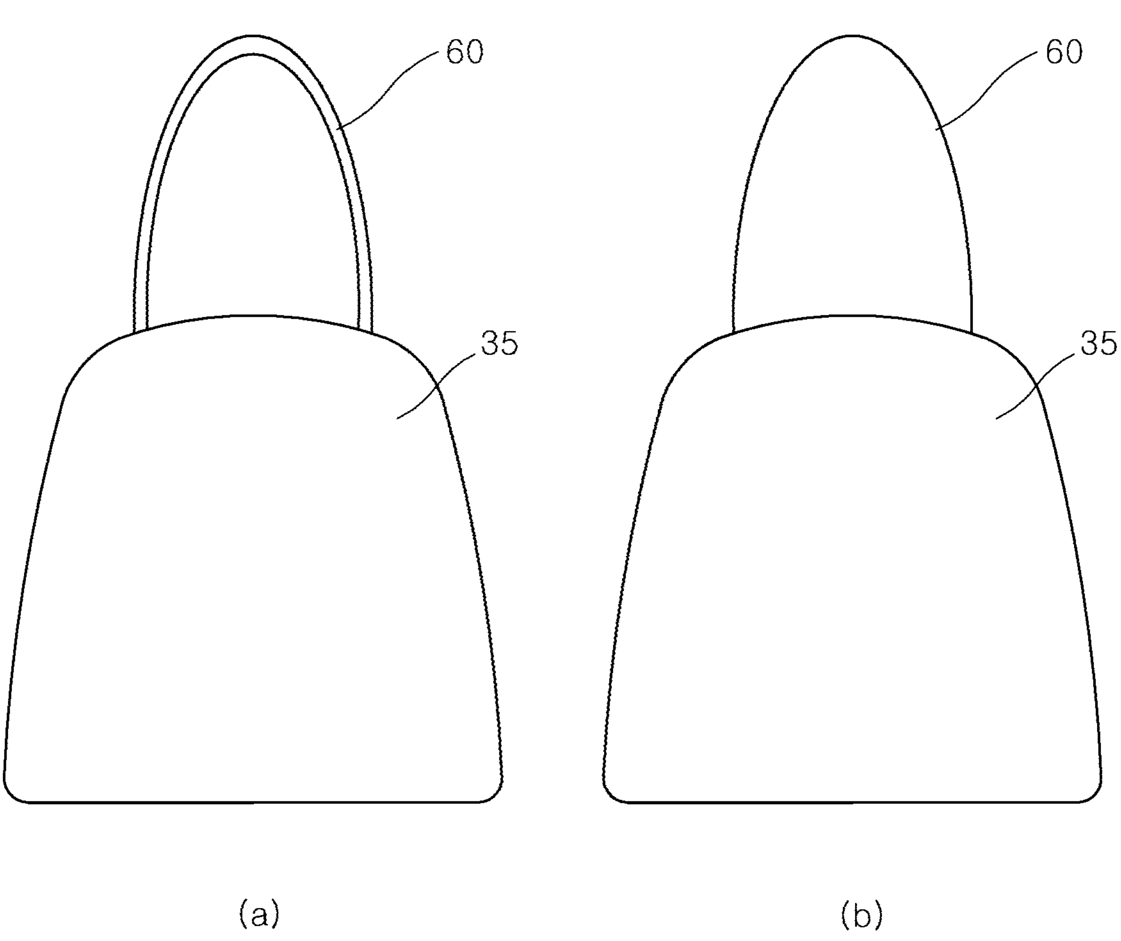

FIG. 18 shows a plan view of an oral device which comprises a main body (35) where the body (10) and the connecting portion (30) are integrally formed. According to the oral device of FIG. 18, the main body (35) presses the tongue to relax the intrinsic tongue muscles, move the floor of mouth upward, and consequently close the oropharynx, thereby facilitating the breathing through the nasopharynx.

Although it is illustrated that the oral device of FIG. 18 comprises a connecting handle (60) for user's convenience and safety, the connecting handle (60) may not be provided. The connecting handle (60) can be made in the form of a strap as shown in FIG. 18(*a*) and can be connected to a separate element such as a user's clothing or a helmet. The connecting handle (60) can be made of a soft material, a flexible material, or a hard material. The shape, size, thickness, and the like of the connecting handle can be variously determined according to requirements. The connecting handle (60) can be a form of a plate.

Figure 19:
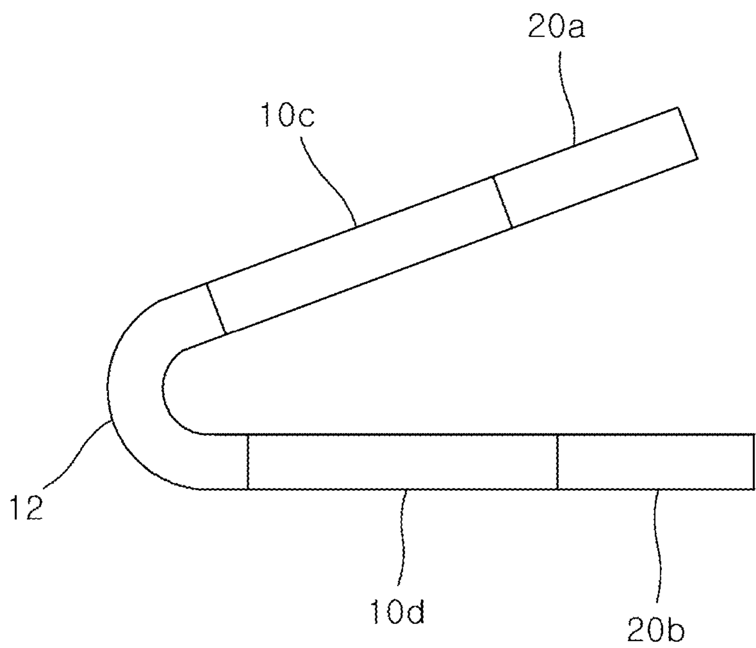
FIG. 19 is a side view of the oral device of an embodiment of the present disclosure.

FIG. 19 shows a side view of an oral device wherein the body (10) is separated into an upper part and the lower part which receive the upper tooth and the lower tooth, respectively. The body (10) comprises a first portion (10*c*) which is provided in the upper side of the oral cavity, i.e., in the upper tooth side, and a second portion (10*d*) which is provided in the lower side of the oral cavity, i.e., in the lower tooth side. The first portion (10*c*) and the second portion (10*d*) are connected at the front end (12) to prevent the mouth from opening. Although it is illustrated in FIG. 19 that the first and second portions are connected at the front end, the portions (10*c*, 10*d*) can be connected at the other position, for example, middle position. The first and second portions may not be connected to each other.

Although it is illustrated in FIG. 19 that a wing (20*a*) extends from the first portion (10*c*) and a wing (20*b*) extends from the second portion (10*d*), the wing can extend from only one of the first portion (10*c*) and the second portion (10*d*).

The oral device of the present disclosure can be connected to various external devices. The external device can be, for example, a container which contains an edible liquid. The oral device of the present disclosure can be fastened to, for example, an opening of a bottle which contains an edible liquid. In that case, the user can easily breathe while the user drinks the liquid.

Figure 23:
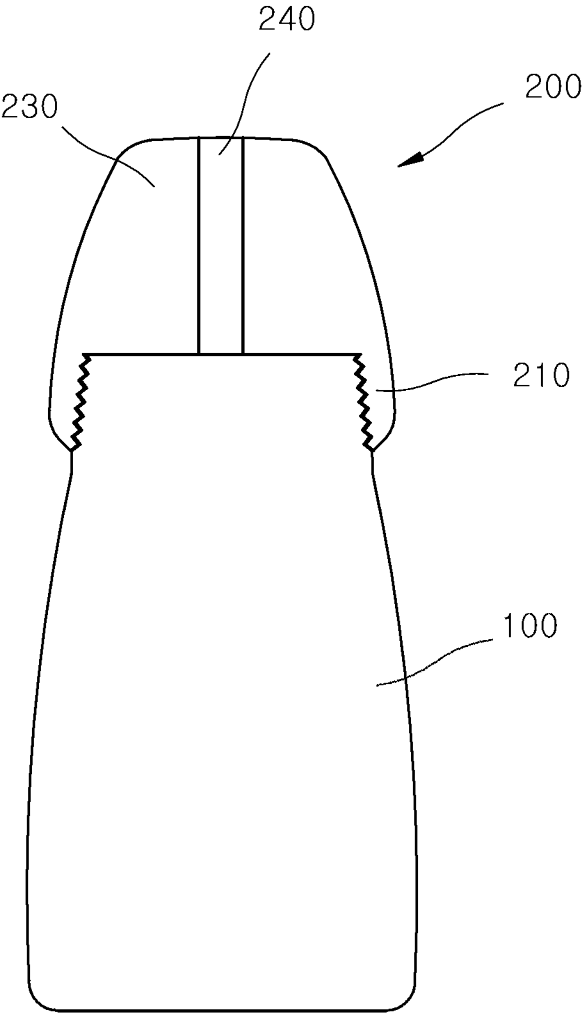
FIG. 23 shows a liquid container where the oral device of the present disclosure is fastened.

FIG. 23 shows a side view of a container where an intermediary drinking device of the present disclosure is fastened. The term "intermediary drinking device" is used for easy explanation but the intermediary drinking device is a kind of the oral device of the present disclosure. The intermediary drinking device comprises a body (210), a connecting portion (230) and a liquid passageway (240). The fastening portion can be a screw fastener, a forced fit fastener, or the like. The body (210) can be directly connected to the container (100) without a fastener.

Although it is illustrated that the liquid passageway (240) extends to the upper side of the oral device from the upper side of the container along a height direction, the passageway can be an opening formed in the body (210).

Figure 24:
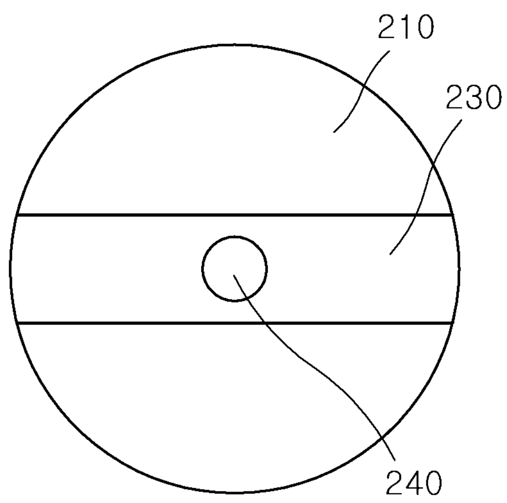
FIG. 24 is a plan view of the oral device shown in FIG. 23.

FIG. 24 shows a plan view of the intermediary drinking device (200) of FIG. 23. When a user puts the intermediary drinking device (200) in the mouth and drinks an edible liquid, the connecting portion (230) enters the oral cavity to prevent the lips from moving forward, thereby pushing the inner muscles of the cheek outward; and to relax the intrinsic tongue muscles, thereby moving the floor of mouth upward and moving the soft palate downward. According to the muscle transition, the oropharynx is closed. In consequence, the breathing through nasopharynx and continuous breathing can be easily achieved while drinking.

Figure 25:
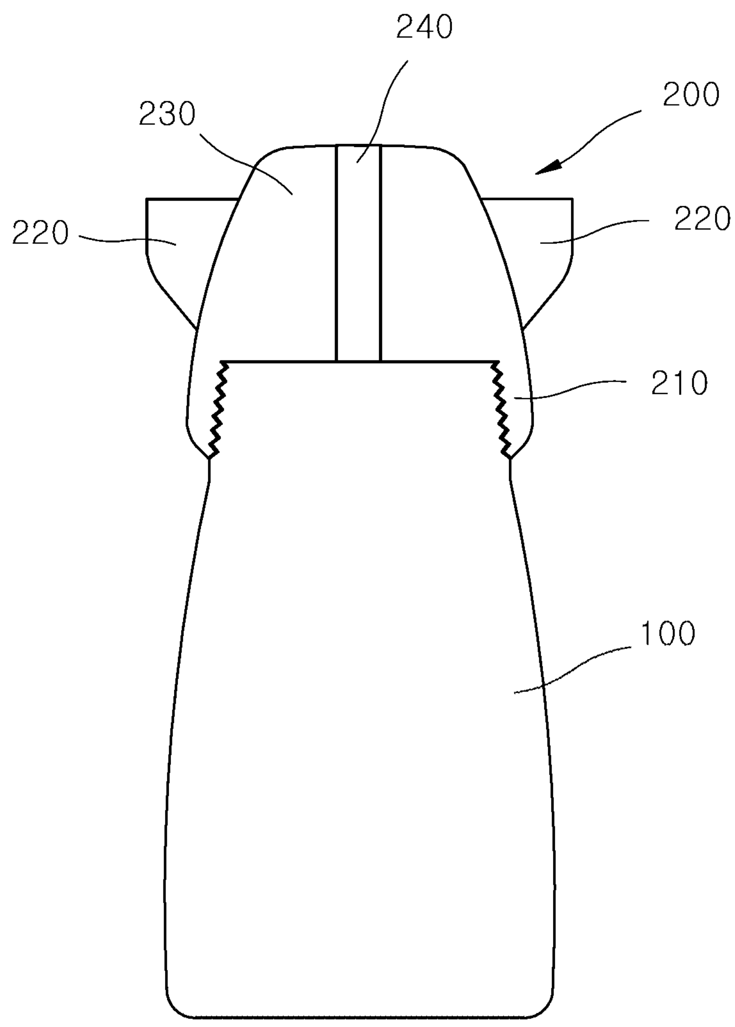
FIG. 25 shows a liquid container where the oral device of an embodiments of the present disclosure is fastened.
Figure 26:
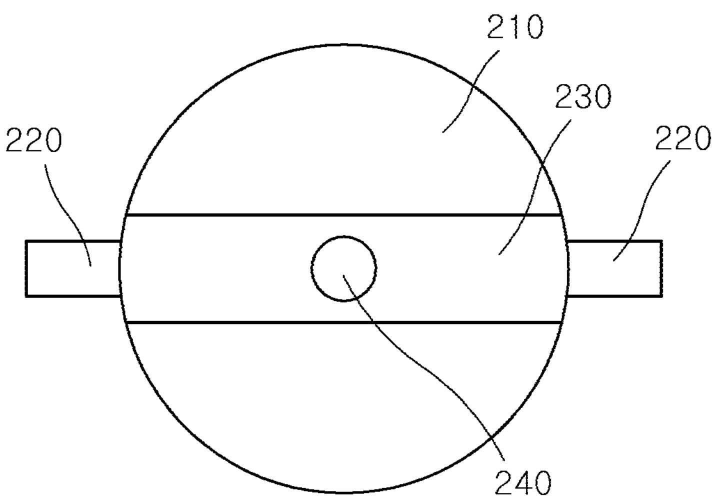
FIG. 26 is a plan view of the oral device shown in FIG. 25.

FIG. 25 shows a side view of a liquid container (100) where an intermediary drinking device (200) of a different aspect of the present disclosure is fastened; and FIG. 26 shows a plan view of the intermediary drinking device (200) shown in FIG. 25. The device is different from the device shown in FIG. 24 in that it further comprises a wing (220) which pushes the inner muscles of the cheek outward. Because the intermediary drinking device (200) further comprises the wing (220), the breathing through the nasopharynx is more facilitated.

Although it is illustrated in FIGS. 25 and 26 that the intermediary drinking device (200) comprises the connecting portion (230) and the wing (220), the device can comprise only the wing (220). The shape, size, thickness, and the like of the wing (220) can be variously determined according to requirements.

Figure 27:
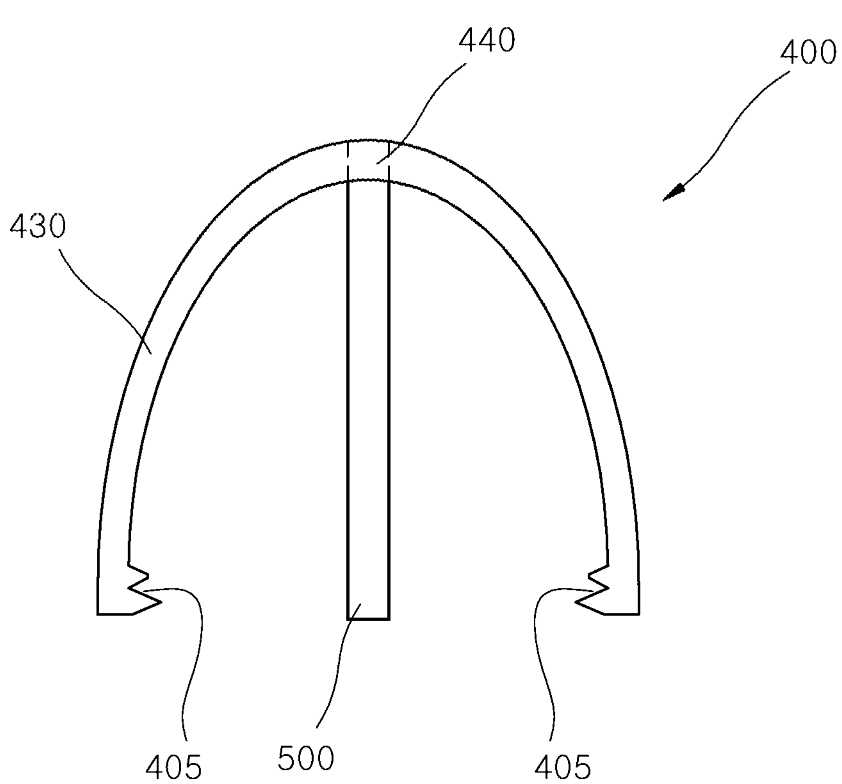
FIG. 27 is a side view of the oral device of another embodiment of the present disclosure.
Figure 28:
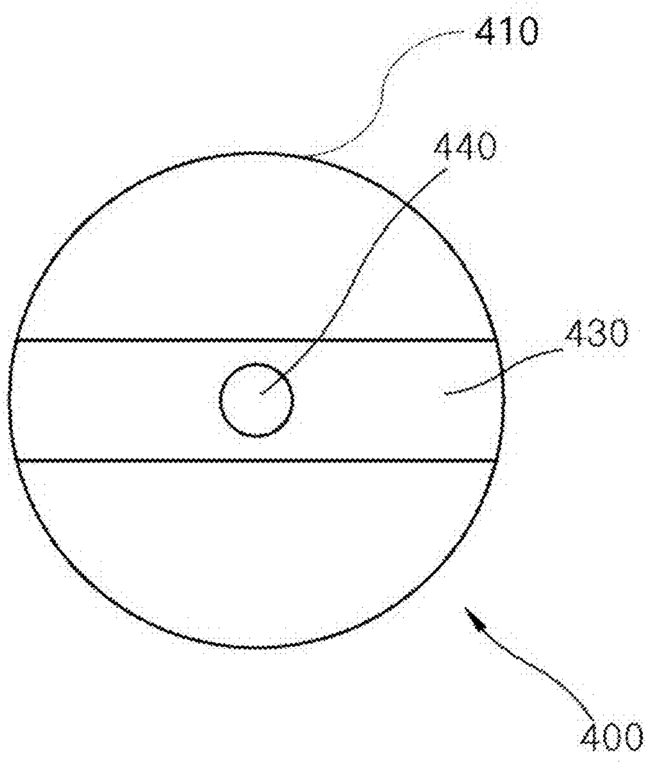
FIG. 28 is a plan view of the oral device shown in FIG. 27.

FIG. 27 shows a side sectional view of an oral device (400; intermediary drinking device) according to another embodiment of the present disclosure; and FIG. 28 shows a plan view of the oral device (400) shown in FIG. 27.

The oral device (400) of FIG. 27 can be connected to an external device for example, a container where an edible liquid is contained. The oral device (400) comprises a connecting portion (430), a fastener (405) and a liquid passageway (500). The liquid passageway (500) can be, for example, a straw. The fastener (405) can be a screw fastener or a forced fit fastener. When a user drinks the edible liquid contained in a container where the oral device (400) shown in FIG. 27 is fastened, the connecting portion (430) prevents the lips from moving forward and presses the tongue to relax the intrinsic tongue muscles, thereby facilitating the breathing through the nasopharynx.

Figure 29:
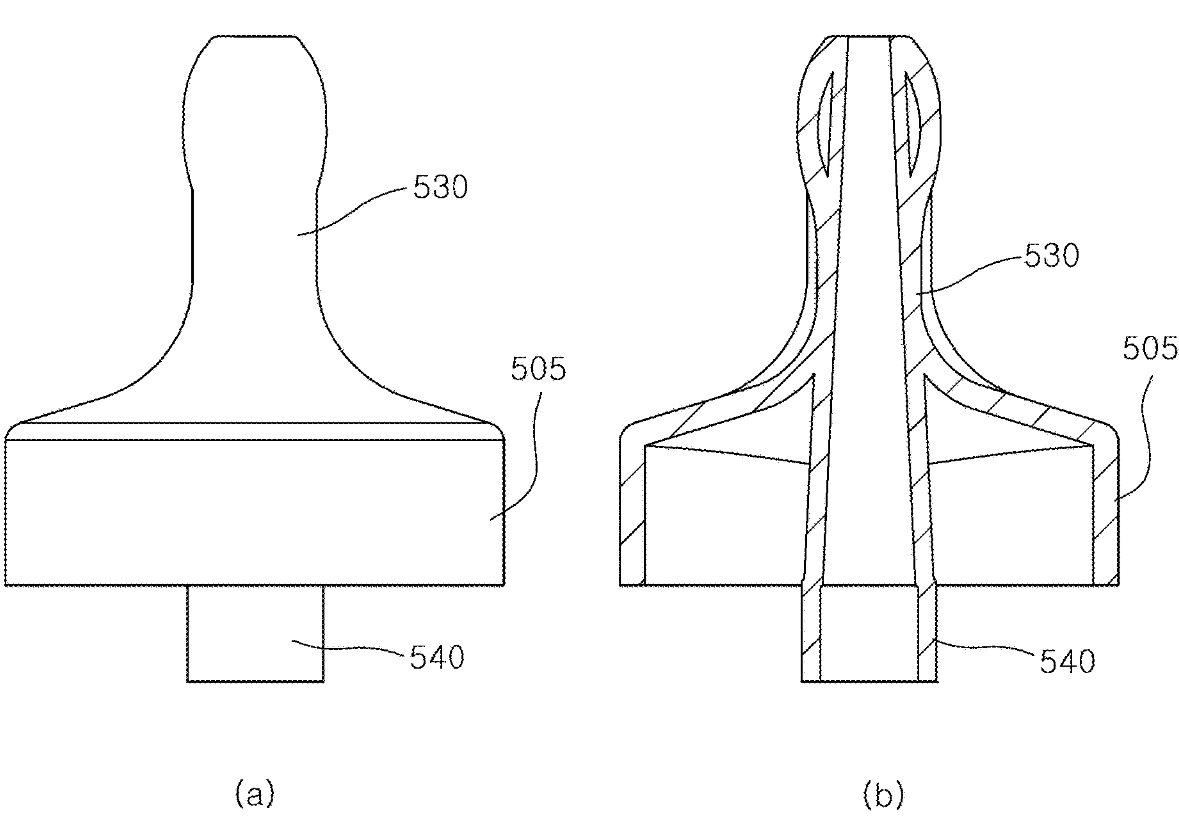
FIG. 29 is a side view of the oral device of another embodiment of the present disclosure.

FIG. 29(*a*) shows a side view of an oral device according to the different embodiments of the present disclosure; FIG. 29(*b*) shows the cross-sectional view of the oral device; and FIG. 30 shows a front cross-sectional view of the oral device.

Figure 30:
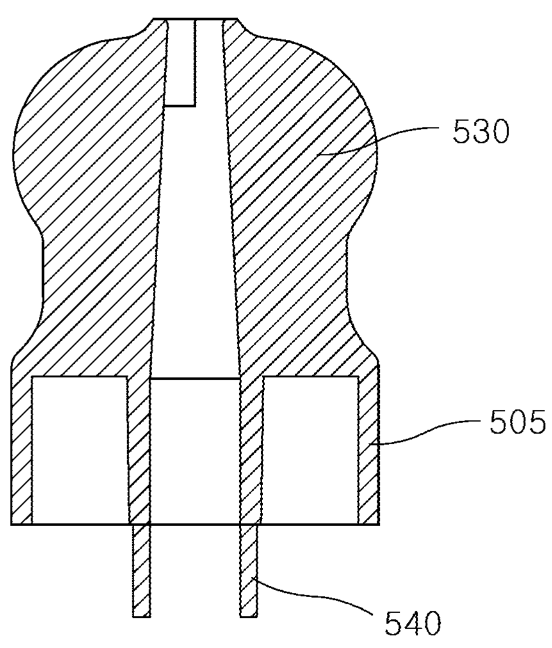
FIG. 30 is a front view of the oral device shown in FIG. 29.

The oral device shown in FIGS. 29 and 30 comprises a connecting portion (530), a fastener (505) and a liquid passageway (540). The liquid passageway (540) further extends toward the liquid container to protrude under the fastener (505) of the oral device. The length of the liquid passageway (540) can be variously determined according to requirements. The end of the liquid passageway (540) can be placed inside the oral device or can extend more than shown in FIG. 29. Although it is illustrated that the liquid passageway (540) linearly extends, the extending line of the passageway (54) can be variously determined to be for example, spiral or bent as part of an arc. Further, the liquid passageway (540) can be provided in plurality. Alternatively, the liquid passageway (540) can be connected to a separate straw.

The connecting portion (530) of the oral device of FIG. 29 prevents the lips from moving forward; and presses the tongue to relax the intrinsic tongue muscles, thereby facilitating the breathing through the nasopharynx.

Figure 31:
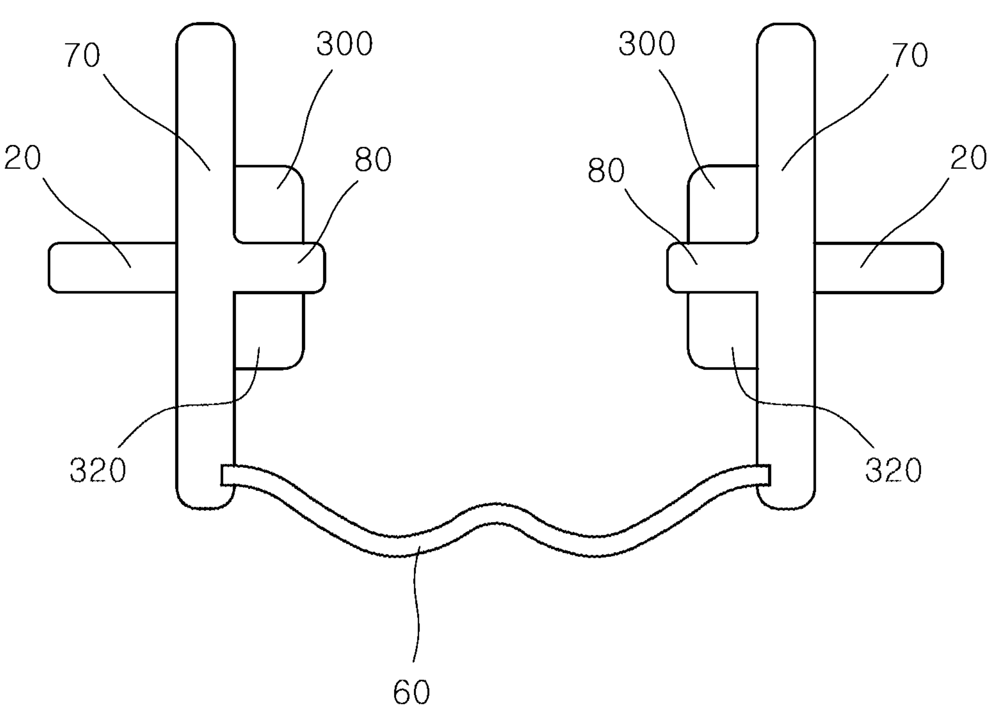
FIG. 31 is a front view of the oral device of another embodiment of the present disclosure.

FIG. 31 shows a front view of an oral device according to the different aspect of the present disclosure. The oral device of FIG. 31 comprises a side body (70) disposed to be contact with a tooth in the outside of tooth, an inner extending portion (80) which extends inwardly from the side body (70) to be engaged between the upper and lower tooth; at least one wing (20) which laterally extends from the side body (70) to push the cheek muscles outward; and a connecting portion (60) connecting the side bodies (70). The side body (70) can be provided in a pair as shown in FIG. 31; can be provided in a single body; or provided in more than three bodies. The side body (70) can be disposed to be contact with the lateral side of a tooth. The connecting portion (60) can connect the side bodies (70) outside of an oral cavity or can connect the side bodies (70) inside the oral cavity.

The upper side and the lower side of the inner extending portion (80) can be engaged between the upper tooth (300) and the lower tooth (320). The inner extending portion (80) extends inwardly so as to press the tongue, thereby relaxing the intrinsic tongue muscles.

The oral device of the present disclosure pushes the cheek muscles outward to prevent the lips from moving forward and to prevent the soft palate from closing the nasopharynx; presses the tongue to relax the intrinsic tongue muscles, thereby allowing the extrinsic tongue muscle to pull the intrinsic tongue muscle outward and rearward. Consequently, the floor of mouth moves upward, and the soft palate moves downward to close the fauces and the oropharynx, thereby facilitating the breathing through the nasopharynx. Thus, the oral device of the present disclosure resolves the problems such as hypoxia, apnea, breathing disorders, snoring, otitis media, a deformation of dental arrangement caused by wrong movements of tongue, mental distractions, dysphonia, gas pain, a deterioration of athletic performance, and the like.

Although the present disclosure has been described with reference to accompanying drawings, the scope of the present disclosure is determined by the claims described below and should not be interpreted as being restricted by the embodiments and/or drawings described above. It should be clearly understood that improvements, changes, and modifications of the present disclosure disclosed in the claims and apparent to those skilled in the art also fall within the scope of the present disclosure. Accordingly, this description is to be taken only by way of example and not to otherwise limit the scope of the embodiments herein.

What is claimed is:

1. An oral device consisting essentially of:

a body configured to depress a tongue, wherein at least a portion of the body is configured to be disposed inside an oral cavity; and non-vertically elongated wings configured to push cheek muscles outward at a second molar or anterior to the second molar between an incisor and the second molar, wherein the body is configured to downwardly press the tongue at an anterior portion of a canine or a second premolar, or at or between an incisor and a second premolar to relax intrinsic tongue muscles, wherein the body is configured to pull a floor of the tongue and other extrinsic tongue muscles laterally rearward and to move soft palate downward, thereby allowing oropharynx to close and nasopharynx to open, and wherein the wings are configured to prevent lips from protruding forward and to push at least one of palatoglossus or palatopharyngeus downward and outward, thereby allowing oropharynx to close and nasopharynx to open.

2. The oral device according to claim 1, wherein the body is separated into at least two parts.

3. The oral device according to claim 2, wherein the body comprises:

a first portion which is configured to be provided in upper tooth; and a second portion which is configured to be provided in lower tooth, wherein the first portion and the second portion are configured to be connected to each other to prevent lips and cheek muscles from collapsing inward.

4. The oral device according to claim 3, wherein the first portion and the second portion are configured to be connected at front side of the oral cavity, thereby preventing the oropharynx from opening and preventing the nasopharynx from closing.

5. The oral device according to claim 1, wherein at least a portion of the body is configured to conform to teeth arrangements.

6. The oral device according to claim 5, wherein the body comprises:

a tooth receiver which is configured to receive at least a portion of tooth.

7. The oral device according to claim 1, wherein the body comprises:

a side body which is configured to be disposed on a side of tooth from outside of the tooth; and an inner extending portion which extends inwardly from the side body to be configured to be engaged with upper tooth and lower tooth, wherein the wings laterally extend from the side body.

8. The oral device according to claim 7, wherein the inner extending portion is configured to press a tongue, thereby relaxing intrinsic tongue muscles, thereby preventing the oropharynx from opening and preventing the nasopharynx from closing.

9. The oral device according to claim 1, wherein the body is integral with the wings.

* * * * *